US007700528B2

(12) United States Patent
Wei et al.

(10) Patent No.: US 7,700,528 B2
(45) Date of Patent: *Apr. 20, 2010

(54) MULTI-PHASE PERSONAL CARE COMPOSITION COMPRISING A STABILIZING PERFUME COMPOSITION

(75) Inventors: Karl Shiqing Wei, Mason, OH (US); Rebecca Ann Taylor, Cincinnati, OH (US); Edward Dewey Smith, III, Mason, OH (US); Zerlina Gudzar Dubois, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 232 days.

This patent is subject to a terminal disclaimer.

(21) Appl. No.: 11/591,240

(22) Filed: Nov. 1, 2006

(65) Prior Publication Data

US 2007/0135319 A1 Jun. 14, 2007

Related U.S. Application Data

(60) Provisional application No. 60/732,312, filed on Nov. 1, 2005.

(51) Int. Cl.
*C11D 3/50* (2006.01)
*A61K 8/00* (2006.01)

(52) U.S. Cl. .............. 510/101; 510/119; 510/130; 510/133; 510/141; 510/146; 424/65; 424/70.1; 424/78.02; 424/76.4; 424/401; 512/2

(58) Field of Classification Search ............. 510/101, 510/119, 130, 133, 141, 146; 424/65, 70.1, 424/78.02, 76.4, 401; 512/2

See application file for complete search history.

(56) References Cited

U.S. PATENT DOCUMENTS

| 2,658,072 | A | 11/1953 | Kosmin |
| 3,929,678 | A | 12/1975 | Laughlin et al. |
| 4,159,028 | A | 6/1979 | Barker |
| 4,335,103 | A | 6/1982 | Barker |
| 4,966,205 | A | 10/1990 | Tanaka |
| 4,980,155 | A | 12/1990 | Shah |
| 5,059,414 | A | 10/1991 | Dallal |
| 5,304,334 | A | 4/1994 | Lahanas |
| 5,612,307 | A | 3/1997 | Chambers |
| 5,804,538 | A | 9/1998 | Wei |
| 5,891,833 | A | 4/1999 | Wei |
| 6,213,166 | B1 | 4/2001 | Thibiant et al. |
| 6,245,344 | B1 | 6/2001 | Thibiant |
| 6,335,312 | B1 | 1/2002 | Coffindaffer et al. |
| 6,362,159 | B1 | 3/2002 | Aguadisch |
| 6,367,519 | B2 | 4/2002 | Thibiant |
| 6,516,838 | B2 | 2/2003 | Thibiant |
| 6,534,456 | B2 | 3/2003 | Hayward |
| 6,534,457 | B2 | 3/2003 | Mitra |
| 6,869,923 | B1 | 3/2005 | Cunningham |
| 6,903,057 | B1 | 6/2005 | Tsaur |
| 6,906,016 | B1 | 6/2005 | Tsaur |
| 2002/0032147 | A1 | 3/2002 | Foley |
| 2003/0053974 | A1 | 3/2003 | Shefer |
| 2003/0134771 | A1 | 7/2003 | Ellson |
| 2004/0057920 | A1 | 3/2004 | Focht et al. |
| 2004/0092414 | A1* | 5/2004 | Clapp et al. ............. 510/130 |
| 2004/0092415 | A1 | 5/2004 | Focht et al. |
| 2004/0092425 | A1* | 5/2004 | Boutique et al. ......... 510/466 |
| 2004/0219119 | A1 | 11/2004 | Wei et al. |
| 2004/0223991 | A1 | 11/2004 | Wei et al. |
| 2004/0248749 | A1 | 12/2004 | Mitra |
| 2005/0003975 | A1* | 1/2005 | Browne et al. ........... 510/101 |
| 2005/0043208 | A1 | 2/2005 | Bettiol |
| 2005/0124530 | A1 | 6/2005 | Creutz |
| 2005/0143282 | A1 | 6/2005 | Creutz |
| 2005/0192187 | A1* | 9/2005 | Wagner et al. ........... 510/130 |
| 2005/0192188 | A1* | 9/2005 | Wagner et al. ........... 510/130 |
| 2005/0192189 | A1* | 9/2005 | Wagner et al. ........... 510/130 |
| 2006/0079417 | A1* | 4/2006 | Wagner et al. ........... 510/130 |
| 2006/0079418 | A1* | 4/2006 | Wagner et al. ........... 510/130 |
| 2006/0079420 | A1* | 4/2006 | Wagner et al. ........... 510/130 |
| 2006/0079421 | A1* | 4/2006 | Wagner et al. ........... 510/130 |
| 2007/0020214 | A1 | 1/2007 | Muller |
| 2007/0071780 | A1* | 3/2007 | Dubois et al. ............ 424/401 |
| 2007/0117729 | A1* | 5/2007 | Taylor et al. ............ 510/130 |
| 2007/0141001 | A1* | 6/2007 | Clapp et al. ............. 424/63 |
| 2007/0280976 | A1* | 12/2007 | Taylor et al. ............ 424/401 |

FOREIGN PATENT DOCUMENTS

| DE | 10340348 A1 | 3/2005 |
| WO | WO 99/62477 A1 | 12/1999 |
| WO | WO 2006/132974 | 12/2006 |

OTHER PUBLICATIONS

National Cancer Institute FactSheet, Formaldehyde and Cancer: Questions and Answers, Jul. 30, 2004, pp. 1-6.*
C.D. Vaughan, "Solubility, Effects in Product, Package, Penetration and Preservation," Cosmetics and Toiletries, vol. 103, Oct. 1988.
International Search Report dated Mar. 9, 2007, U.S. Appl. No. 11/591,240 filed Nov. 1, 2006, 124 pages.

* cited by examiner

*Primary Examiner*—Douglas Mc Ginty
(74) *Attorney, Agent, or Firm*—Mark A. Charles

(57) ABSTRACT

A method of stabilizing a multiphase composition is described. The composition comprises a structured surfactant phase, a benefit phase and a perfume comprising perfume raw materials. The method comprises a step of selecting at least 70% of the perfume raw materials that have a ClogP of greater than 1.8.

20 Claims, No Drawings

MULTI-PHASE PERSONAL CARE COMPOSITION COMPRISING A STABILIZING PERFUME COMPOSITION

CROSS REFERENCE TO RELATED APPLICATION

This application claims the benefit of U.S. Provisional Application No. 60/732,312, filed Nov. 1, 2005.

FIELD OF THE INVENTION

The present invention relates to a structured personal care composition comprising a perfume composition.

BACKGROUND OF THE INVENTION

Personal care compositions are well known and widely used. Desirable personal care composition must meet a number of criteria. For example, in order to be acceptable to consumers, a personal care composition must exhibit good cleaning properties, must exhibit good lathering characteristics, must be mild to the skin (not cause drying or irritation) and preferably should even provide a conditioning benefit to the skin. Some consumers choose a personal care composition for both the odor of the product itself, as well as, the residual odor the composition leaves on the skin or hair. Perfumes contain individual components called perfume raw materials or PRMs, which add to the perfume's scent. Certain PRMs are more volatile and provide a scent or "bloom" when the bottle is opened, or when used in the shower. Other PRMs tend to deposit on the skin and can last longer, providing a residual benefit, or perfume longevity. These PRMs are sometimes called 'base notes' of a fragrance.

However, some perfumes and perfume raw materials can affect other qualities of the composition, such as viscosity, lather and visual appearance. For example, the perfume and perfume raw materials can interact with surfactant micelles, increasing viscosity of the personal care composition and reducing the lather obtained from the personal care composition. As well, compositions that comprise surfactant also have limited ability to absorb perfume, and high levels of perfume can form a separate, turbid phase in an otherwise transparent composition making the composition visually unattractive to some consumers. Therefore, some personal care compositions and multiphase personal care compositions with perfumes often do not maintain their viscosity so as to provide consistent dispensing and not separate into bulk phases as the compositions age.

Accordingly, the need still remains for multiphase personal care compositions with perfumes which remain stable.

SUMMARY OF THE INVENTION

The present invention relates to a method of stabilizing a multiphase composition. The composition comprises a structured surfactant phase, a benefit phase and perfume comprising perfume raw material. The method comprises a step of selecting at least 70% of the perfume raw materials that have a ClogP of greater than 1.8.

The present invention also relates to a multiphase personal care composition comprising a structured surfactant phase, a benefit phase and perfume comprising perfume raw materials; wherein at least 70%, of the perfume raw materials have a Clog P greater than 1.8.

The present invention also relates to a personal care composition comprising a structured surfactant phase, a benefit phase, a preservative, and perfume comprising perfume raw materials; the preservative being substantially free of formaldehyde; wherein at least 70% of the perfume raw materials have a Clog P greater than 1.8.

The present invention also relates to a personal care composition comprising a structured surfactant phase, a benefit phase and perfume comprising perfume raw materials; wherein less than 30%, by weight of said perfume, of said perfume raw materials are selected from the group consisting of benzaldehyde dimethyl acetal, benzaldehyde glyceryl acetal, cinnamic alcohol, cinnamic aldehyde dimethyl acetal, cis-3-hexenal, diethyl malonate, dihydro coumarin, ethyl butanoate, ethyl methyl dioxolane acetate (2-Me, 1,3-dioxol-2-acet.), ethyl vanillin—see 4-hydroxy 3-ethoxybenzaldehyde, heliotropine dimethyl acetal, hexanol (2-, 3-), hexenol (all isomers), hexenone (1-hexen-3-one, 4-hexen-3-one, 5-hexen-2-one)), hexyl cinnamate, hydrocinnamic aldehyde, hydrocinnamyl alcohol, hydroquinone, hydroquinone monomethyl ether, linalool oxide, methyl phenylacetate, nonenal (all isomers), o-anisaldehyde & m- & p- also, phenethyl alcohol, phenoxyacetaldehyde, phenylacetaldehyde ethyleneglycol acetal, prenyl acetate, propylene glycol, sinensal, triethyl citrate, valeraldehyde, valeric acid, valerolactone, vanillic acid, vanillin acetate, vanillin isobutyrate, vanillyl alcohol, vanillylidene acetone and mixtures thereof.

The Inventors believe that by choosing perfume raw materials for the composition, which more hydrophobic, stability of multi-phase personal care compositions is enhanced.

DETAILED DESCRIPTION OF THE INVENTION

The term "ambient conditions" as used herein, refers to surrounding conditions at one (1) atmosphere of pressure, 50% relative humidity, and 25° C.

By the term "multi-phase" or "multi-phase" as used herein, is meant that the phases of the present compositions occupy separate but distinct physical spaces inside the package in which they are stored, but are in direct contact with one another. In one preferred embodiment of the present invention, the "multi-phase" personal care compositions can comprise at least two visually distinct phases which are present within the container as a visually distinct pattern. The pattern results from the combination of the "multi-phase" composition by a process herein described. The "patterns" or "patterned" include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. Preferably the pattern is selected from the group consisting of striped, geometric, marbled, and combinations thereof. The phases may be various different colors, and/or include particles, glitter or pearlescent agents in at least one of the phases in order to offset its appearance from the other phase(s) present.

The term "multi-phase personal care composition" as used herein, refers to compositions intended for topical application to the skin or hair. Non-limiting examples of personal care compositions are selected from the group consisting of a skin care lotion, a bar soap, a body wash, a shampoo, conditioner, an in-shower body moisturizer and mixtures thereof.

The term "structured," as used herein means having a rheology that confers stability on the multi-phase composition. The degree of structure is determined by the Yield Stress and Zero Shear Viscosity Method and by the Ultracentrifugation Method, both described hereafter. When a phase is a structured phase, typically it has a Yield Stress of greater than about 0.1 Pascal (Pa), more preferably greater than about 0.5 Pa, even more preferably greater than about 1.0 Pa, still more preferably greater than about 2.0 Pa, still even more preferably greater than about 3 Pa, and even still even more preferably greater than about 5 Pa as measured by the Yield Stress and Zero Shear Viscosity Method described hereafter. When a phase is a structured phase, it may also typically have a Zero Shear Viscosity of at least about 500 Pascal-seconds (Pa-s), preferably at least about 1,000 Pa-s, more preferably at least about 1,500 Pa-s, even more preferably at least about 2,000 Pa-s. Accordingly, when a surfactant phase or a surfactant phase of the multi-phase composition of the present invention is structured, it has a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%.

The term "substantially free of formaldehyde" as used herein means the total amount of formaldehyde in the composition is less than about 0.1%, preferably the total amount of formaldehyde in the composition is less than about 0.05%, more preferably the total amount of formaldehyde in the composition is less than about 0.01%, and most preferably the total amount of formaldehyde in the composition is about 0%.

The term "surfactant component" as used herein means the total of all anionic, nonionic, amphoteric, zwitterionic and cationic surfactants in a phase, excluding ingredients used to facilitate manufacturing said surfactants, e.g., water, excess bases and acids, preservatives, etc.

The term "visually distinct phase" as used herein, refers to a region of the multi-phase personal care composition having one average composition, as distinct from another region having a different average composition, wherein the regions are visible to the unaided naked eye. This would not preclude the distinct regions from comprising two similar phases where one phase could comprise pigments, dyes, particles, and various optional ingredients, hence a region of a different average composition. A phase generally occupies a space or spaces having dimensions larger than the colloidal or sub-colloidal components it comprises. A phase may also be constituted or re-constituted, collected, or separated into a bulk phase in order to observe its properties, e.g., by centrifugation, filtration or the like.

The present invention relates to a method of stabilizing a multiphase composition. The composition comprises a structured surfactant phase, a benefit phase and perfume comprising perfume raw materials. The method comprises a step of selecting at least 70% of the perfume raw materials that have a ClogP of greater than 1.8.

The present invention also relates to a multiphase personal care composition comprising a structured surfactant phase, a benefit phase and perfume comprising perfume raw materials; wherein at least 70% of the perfume raw materials have a Clog P greater than 1.8.

The present invention also relates to a personal care composition comprising a structured surfactant phase, a benefit phase, a preservative, and perfume comprising perfume raw materials; the preservative being substantially free of formaldehyde; wherein at least 70% of the perfume raw materials have a Clog P greater than 1.8.

A perfume raw material (PRM) is characterized by its lipophilicity as determined by its calculated $\log_{10}$(octanol/water partition coefficient), or ClogP. The ClogP of a PRM is the ratio between its equilibrium concentrations in octanol and in water in a mixture comprising only octanol, water and the PRM. The preferred PRMs of this invention have ClogP at 25° C. of greater than about 1.8.

In the composition and method of the present invention, at least 70% of the PRMs have a ClogP of greater than 1.8. In other embodiments of the composition and method of the present invention, at least 80% of the PRMs have a ClogP of greater than 1.8. In other embodiments of the composition and method of the present invention, at least 85% of the PRMs have a ClogP of greater than 1.8. In other embodiments of the composition and method of the present invention, at least 90% of the PRMs have a ClogP of greater than 1.8. In other embodiments of the composition and method of the present invention, at least 95% of the PRMs have a ClogP of greater than 1.8.

TABLE 1

Examples of Perfume Raw Materials with high ClogP Values greater than 1.8

| Chemical Name | Clog P |
|---|---|
| Gamma-Nonalactone | 1.85 |
| Florol | 2.00 |
| Isoeugenol | 2.45 |
| Cis Jasmone | 2.905 |
| Dihydromyrcenol | 3.004 |
| Citral | 3.169 |
| Geraniol | 3.279 |
| Linalool | 3.281 |
| Citronellol | 3.382 |
| Cymal | 3.722 |

The Inventors believe that stability of a personal care composition can be enhanced if one chooses to use PRMs in personal care composition that have a higher ClogP and are more hydrophobic and to avoid PRMs that have a lower ClogP and are more hydrophilic. Thereof, the present invention also relates to a personal care composition comprising a structured surfactant phase, a benefit phase and perfume comprising perfume raw materials; wherein less than 30%, by weight of said perfume, of said perfume raw materials are selected from the group consisting of anisyl acetate, benzaldehyde dimethyl acetal, benzaldehyde glyceryl acetal, benzyl methyl ether, cinnamic alcohol, cinnamic aldehyde, cinnamic aldehyde dimethyl acetal, cinnamyl formate, cis-3-hexenal, diethyl malonate, dihydro coumarin, ethyl butanoate, ethyl methyl dioxolane acetate (2-Me, 1,3-dioxol-2-acet.), ethyl vanillin—see 4-hydroxy 3-ethoxybenzaldehyde, heliotropine dimethyl acetal, hexanol (2-, 3-), hexenol (all isomers), hexenone (1-hexen-3-one, 4-hexen-3-one, 5-hexen-2-one)), hexyl cinnamate, hydrocinnamic aldehyde, hydrocinnamyl alcohol, hydroquinone, hydroquinone monomethyl ether, 1-Carveol, linalool oxide, methyl phenylacetate, methyl jasmonate, methylcoumarin (6-, 7-, isomers), nonenal (all isomers), o-anisaldehyde & m- & p- also, phenethyl alcohol, phenoxyacetaldehyde, phenylacetaldehyde ethyleneglycol acetal, prenyl acetate, propylene glycol, sinensal, triethyl citrate, valeraldehyde, valeric acid, valerolactone, vanillic acid, vanillin acetate, vanillin isobutyrate, vanillyl alcohol, vanillylidene acetone and mixtures thereof. In some embodiments, the personal care composition can comprise less than 25%, less than 20%, less than 15%, less than 12%, less than 10%, less than 8%, less than 5% , less than 3% and even less than 1% of %, by weight of said perfume, of said perfume raw materials are selected from the group consisting of anisyl acetate, benzaldehyde dimethyl acetal, benzaldehyde glyceryl acetal, benzyl methyl ether, cinnamic alcohol, cinnamic aldehyde, cinnamic aldehyde dimethyl acetal, cinnamyl formate, cis-3-hexenal, diethyl malonate, dihydro coumarin, ethyl butanoate, ethyl methyl dioxolane acetate (2-Me, 1,3-dioxol-2-acet.), ethyl vanillin—see 4-hydroxy 3-ethoxybenzaldehyde, heliotropine dimethyl acetal, hexanol (2-, 3-), hexenol (all isomers), hexenone (1-hexen-3-one, 4-hexen-3-one, 5-hexen-2-one)), hexyl cinnamate, hydrocinnamic aldehyde, hydrocinnamyl alcohol, hydroquinone, hydroquinone monomethyl ether, 1-Carveol, linalool oxide, methyl phenylacetate, methyl jasmonate, methylcoumarin (6-, 7-, isomers), nonenal (all isomers), o-anisaldehyde & m- & p- also, phenethyl alcohol, phenoxyacetaldehyde, phenylacetaldehyde ethyleneglycol acetal, prenyl acetate, propylene glycol, sinensal, triethyl citrate, valeraldehyde, valeric acid, valerolactone, vanillic acid, vanillin acetate, vanillin isobutyrate, vanillyl alcohol, vanillylidene acetone and mixtures thereof.

TABLE 2

Examples of Perfume Raw Materials with low ClogP Values

| Chemical Name | ClogP |
|---|---|
| benzaldehyde dimethyl acetal | 1.6 |
| benzaldehyde glyceryl acetal | 0.9 |
| cinnamic alcohol | 1.4 |
| cinnamic aldehyde dimethyl acetal | 1.5 |
| cis-3-hexenal | 1.4 |
| diethyl malonate | 1.1 |
| Dihydro coumarin | |
| ethyl butanoate | 1.8 |
| ethyl methyl dioxolane acetate (2-Me, 1,3-dioxol-2-acet.) | 0.8 |
| ethyl vanillin - see 4-hydroxy 3-ethoxybenzaldehyde | |
| heliotropine dimethyl acetal | 1.0 |
| hexanol (2-, 3-) | 1.7 |
| hexenol (all isomers) | 1.4 |
| hexenone (1-hexen-3-one, 4-hexen-3-one, 5-hexen-2-one)) | 1.0 |
| hexyl cinnamate | 1.5 |
| hydrocinnamic aldehyde | 1.7 |
| hydrocinnamyl alcohol | 1.7 |
| Hydroquinone | 0.9 |
| hydroquinone monomethyl ether | 1.6 |
| Linalool oxide | 1.4 |
| methyl phenylacetate | 1.8 |
| nonenal (all isomers) | 0.9 |
| o-anisaldehyde & m- & p- also | 1.8 |
| phenethyl alcohol | 1.2 |
| phenoxyacetaldehyde | 1.2 |
| phenylacetaldehyde ethyleneglycol acetal | 1.5 |
| prenyl acetate | 1.7 |
| propylene glycol | 1.7 |
| Sinensal | 1.8 |
| triethyl citrate | 1.2 |
| Valeraldehyde | 1.4 |
| valeric acid | 1.4 |
| Valerolactone | 0.7 |
| Vanillic acid | 1.3 |
| Vanillin acetate | 0.7 |
| Vanillin isobutyrate | 1.5 |
| Vanillyl alcohol | 0.3 |
| Vanillylidene acetone | 1.2 |

ClogP is a calculated quantity for a PRM, determined from a mathematical algorithm using molecular substructure or fragment contributions with correction factors. The approach is common in such fields as toxicology, environmental transport, and pharmaceuticals, for example to facilitate development of drugs, especially for topical drugs that interact with lipid bilayers in skin, a molecular mechanism not dissimilar to interaction of PRM molecules with surfactant. Different substructure fragment algorithms exist which can calculate different ClogP values for the same molecule, based on differences in algorithms and/or coefficients, as can be found in scientific literature. For the purposes of our invention, ClogP of a PRM is determined using the algorithm from Advanced Chemistry Development Labs as referenced and updated in the scientific literature (Hansch, C. and Leo, A., Substituent Constants for Correlation Analysis in Chemistry and Biology, Wiley Interscience New York (1979); updated in Leo., A. and Hoekman, D., Perspect. in Drug Discov. & Design, 18, 19 (2000)), using the software Solaris V4.67. The software is published by Daylight Chemical Information Systems, Santa Fe, N. Mex., USA (U.S. phone 505-989-1000) and is downloadable from the web site http://www.daylight.com/download/.

The method of stabilizing a multiphase composition further comprises the step of incorporating a preservative into the multiphase composition wherein the preservative is substantially free of formaldehyde. Preferably, the composition comprises less than 0.01% formaldehyde.

The multi-phase personal care composition of the present invention is typically extrudable or dispensible from a package. The multi-phase personal care compositions typically exhibit a viscosity of from about 1,500 centipoise (cP) to about 1,000,000 cP, as measured by the Viscosity Method as described in copending application Ser. No. 10/841,174 filed on May 7, 2004 titled "Multi-phase Personal Care Compositions."

When evaluating a multi-phase personal care composition, by the methods described herein, preferably each individual phase is evaluated prior to combining, unless otherwise indicated in the individual methodology. However, if the phases are combined, each phase can be separated by centrifugation, ultracentrifugation, pipetting, filtering, washing, dilution, concentration, or combination thereof, and then the separate components or phases can be evaluated. Preferably, the separation means is chosen so that the resulting separated components being evaluated is not destroyed, but is representative of the component as it exists in the multi-phase personal care composition, i.e., its composition and distribution of components therein is not substantially altered by the separation means. Generally, multi-phase compositions comprise domains significantly larger than colloidal dimensions so that separation of the phases into the bulk is relatively easy to accomplish while retaining the colloidal or microscopic distribution of components therein. Preferably, the compositions of the present invention are rinse-off formulations, by which is meant the product is applied topically to the skin or hair and then subsequently (i.e., within minutes) the skin or hair is rinsed with water, or otherwise wiped off using a substrate or other suitable removal means with deposition of a portion of the composition.

The multi-phase personal care compositions of the present invention can comprise at least two visually distinct phases, wherein the composition can have a first structured phase, a second phase, a third phase, a fourth phase and so on. The ratio of a first phase to a second phase is preferably from about 1:99 to about 99:1, preferably from about 90:10 to about 10:90, more preferably from about 80:20 to about 20:80. The preferred pH range of the multi-phase personal care composition is from about 5 to about 8.

The multiphase personal care compositions of the present invention comprise a structured surfactant phase and a benefit phase.

The surfactant component preferably comprises a lathering surfactant or a mixture of lathering surfactants suitable for application to the skin or hair. Suitable surfactants for use herein include any known or otherwise effective cleansing surfactant suitable for application to the skin, and which are otherwise compatible with the other essential ingredients in the multi-phase personal care composition including water.

These surfactants include anionic, nonionic, cationic, zwitterionic, amphoteric surfactants, soap, or combinations thereof. Preferably, anionic surfactant comprises at least 40% of the surfactant component.

The multi-phase personal care composition preferably comprises a structured surfactant phase comprising a surfactant component at concentrations ranging from about 10% to about 21%, more preferably from about 14% to about 20%, by weight of the first phase, i.e. structured surfactant phase.

The surfactant phase preferably comprises a structured domain comprising surfactants. The structured domain enables the incorporation of high levels of benefit components in a separate phase that are not emulsified in the composition while maintaining stability. In a preferred embodiment the structured domain is an opaque structured domain. The opaque structured domain is preferably a lamellar phase. The lamellar phase can provide resistance to shear, adequate yield to suspend particles and droplets and at the same time provides long term stability, since it is thermodynamically stable. The lamellar phase minimizes the need for viscosity modifiers.

Suitable surfactants are described in McCutcheon's, Detergents and Emulsifiers, North American edition (1986), published by allured Publishing Corporation; and McCutcheon's, Functional Materials, North American Edition (1992); and in U.S. Pat. No. 3,929,678 issued to Laughlin, et al. on Dec. 30, 1975.

Preferred linear anionic surfactants for use in the surfactant component of the multi-phase, personal care composition include ammonium lauryl sulfate, ammonium laureth sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, potassium lauryl sulfate, and combinations thereof.

Branched anionic surfactants suitable for the present invention are described in commonly owned U.S. Application Ser. No. 60/680,149 entitled "Structured Multi-phased Personal Cleansing Compositions Comprising Branched Anionic Surfactants" filed on May 12, 2004 by Smith, et al. Branched anionic surfactants include but are not limited to the following surfactants: sodium trideceth sulfate, sodium tridecyl sulfate, sodium $C_{12-13}$ alkyl sulfate, and $C_{12-13}$ pareth sulfate and sodium $C_{12-13}$ pareth-n sulfate. Branched surfactants can be derived from synthetic alcohols such as the primary alcohols from the liquid hydrocarbons produced by Fischer-Tropsch condensed syngas, for example Safol™ 23 Alcohol available from SASOL North America, Houston, Tex.; from synthetic alcohols such as Neodol™ 23 Alcohol available from Shell Chemicals, USA; from synthetically made alcohols such as those described in U.S. Pat. No. 6,335, 312 issued to Coffindaffer, et al. on Jan. 1, 2002. Preparation via $SO_3$ air stream in a falling film reactor is a preferred sulfation process.

Amphoteric surfactants suitable for use in the multi-phase, personal care composition include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, and N-alkyltaurines such as the one prepared by reacting dodecylamine with sodium isethionate according to the teaching of U.S. Pat. No. 2,658, 072 issued to Kosmin, et al. Amphoacetates and diamphoacetates, may also be used. Sodium lauroamphoacetate, disodium lauroamphoacetate are preferred in some embodiments.

Zwitterionic surfactants suitable for use in the multi-phase, personal care composition include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Other zwitterionic surfactants suitable for use in the multi-phase, personal care composition include betaines, including high alkyl betaines such as, coco dimethyl carboxymethyl betaine, cocoamidopropyl betaine, cocobetaine, and carboxymethyl betaine.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, alkanolamides, ethoxylated alcohols and mixtures thereof. In a preferred embodiment the nonionic surfactant is selected from the group consisting of glyceryl monohydroxystearate, steareth-2, isosteareth-2, hydroxy stearic acid, propylene glycol stearate, PEG-2 stearate, sorbitan monostearate, glyceryl stearate, glyceryl laurate, laureth-2, cocamide monoethanolamine, and mixtures thereof.

Mixtures of anionic surfactants may be used in some embodiments, including mixtures of linear and branched surfactants, and anionic surfactants with nonionic, amphoteric, and/or zwitterionic surfactants.

The electrolyte, if used, can be added per se to the multi-phase personal care composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium chloride, ammonium chloride, sodium or ammonium sulfate, and sodium citrate. The electrolyte is preferably added to the surfactant phase of the composition in the amount of from about 0.1% to about 15% by weight, preferably from about 1% to about 6% by weight of the multi-phase personal care composition, but may be varied if required.

In one embodiment of the present invention, the multi-phase, personal care composition comprises a surfactant phase comprising an electrolyte and a surfactant component comprising a mixture of at least one nonionic surfactant, at least one anionic surfactant and at least one amphoteric surfactant. In another embodiment, the surfactant phase can comprise a mixture of surfactants, water, at least one anionic surfactant, an electrolyte, and at least one alkanolamide.

The multi-phase, personal care compositions of the present invention comprises a second phase. A preferred second phase is a benefit phase. The benefit phase in the present invention preferably comprises hydrophobic materials. The benefit phase comprises from about 1% to about 100%, preferably at least about 35%, most preferably at least about 50%, by weight of the benefit phase, of a hydrophobic material. Hydrophobic materials suitable for use in the present invention preferably have a Vaughan Solubility Parameter of from about 5 to about 15 $(cal/cm^3)^{1/2}$, as defined by *Vaughan in Cosmetics and Toiletries*, Vol. 103. Non-limiting examples of hydrophobic materials having VSP values ranging from about 5 to about 15 include the following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product, Package, Penetration and Preservation*, C. D. Vaughan, Cosmetics and Toiletries, Vol. 103, October 1988.

The benefit phase preferably has defined rheological properties as described hereinafter, including selected Consistency value (K) and Shear Index (n). These preferred Theological properties are especially useful in providing the multiphase, personal care compositions with improved deposition of hydrophobic materials. The benefit phase has a Consistency Value (K) from about 5 to about 2,000 Pa-s, preferably from about 30 to about 350 Pa-s. The benefit phase preferably has a Shear Index from about 0.025 to about 0.99, more preferably from about 0.05 to about 0.70.

Nonlimiting examples of hydrophobic materials suitable for use herein can include a variety of hydrocarbons, oils and waxes, silicones, fatty acid derivatives, cholesterol and its derivatives, diglycerides, triglycerides, vegetable oils and derivatives, acetoglyceride esters, alk(en)yl esters, polyglycerol esters, lanolin and its derivatives, wax esters, sterols and phospholipids, petrolatum, mineral oil, triglycerides, alkyl siloxanes, polymethylsiloxanes and methylphenylpolysiloxanes, and combinations thereof.

Examples of suitable benefit phases and description of measuring the values of Consistency (K) and Shear Index (n) are described in U.S. patent application Ser. No. 10/665,670, Publication No. 2004/0057920 A1 entitled Striped liquid personal cleansing compositions containing a cleansing phase and a separate benefit phase" filed by Fact, et al. on Sep. 18, 2003, published on Apr. 4, 2004, U.S. patent application Ser. No. 10/699,469 Publication No. 2004/0092415 A1 entitled "Striped liquid personal cleansing compositions containing a cleansing phase and a separate benefit phase with improved stability" filed by Fact, et al. on Oct. 31, 2003, published on May 13, 2004 and U.S. patent application Ser. No. 10/837,214 Publication No. 2004/0219119 A1 entitled "Visually distinctive multiple liquid phase compositions" filed by Weir, et al. on Apr. 30, 2004, published on Nov. 18, 2004.

The phases of the multi-phase personal care composition, preferably the surfactant phase, can further comprise a polymeric phase structurant. Non-limiting examples of polymeric phase structurant include but is not limited to the following examples: deflocculating polymers, naturally derived polymers, synthetic polymers, crosslinked polymers, block copolymers, nonionic polymers, anionic polymers, associative polymers, oligomers, and copolymers thereof as described in U.S. Patent Application No. 60/628,036 filed on Nov. 15, 2003 by Wagner, et al. titled "Depositable Solids." The polymeric phase structurant can be crosslinked.

The phase of the present compositions, preferably the surfactant phase, optionally can further comprise a liquid crystalline phase inducing structurant, which when present is at concentrations ranging from about 0.5% to about 5% by weight of the phase. Suitable liquid crystalline phase inducing structurants include fatty acids, ester derivatives of fatty acids, fatty alcohols, trihydroxystearin. Preferably, the liquid crystalline phase inducing structurant is selected from lauric acid, trihydroxystearin, and tridecanol.

The multi-phase personal care compositions of the present invention can additionally comprise an organic cationic deposition polymer in the one or more phases as a deposition aid for the benefit agents described herein. Suitable cationic deposition polymers for use in the compositions of the present invention contain cationic nitrogen-containing moieties such as quaternary ammonium or cationic protonated amino moieties. The cationic protonated amines can be primary, secondary, or tertiary amines depending upon the particular species and the selected pH of the multi-phase personal care composition. Suitable cationic deposition polymers useful in the compositions of the present invention are disclosed in the co-pending and commonly assigned U.S. Patent Application No. 60/628,036 filed on Nov. 15, 2003 by Wagner, et al. titled "Depositable Solids." Nonlimiting examples of cationic deposition polymers for use in compositions include polysaccharide polymers, such as cationic cellulose derivatives.

One or more of the phases of the multi-phase personal care composition can comprise a variety of additional optional ingredients such as exfoliant particles, shiny particles, talc, mica, beads. Such optional ingredients are most typically those materials approved for use in cosmetics and that are described in reference books such as the CTFA Cosmetic Ingredient Handbook, Second Edition. The Cosmetic, Toiletries, and Fragrance Association, Inc. 1988, 1992.

Other non limiting examples of these optional ingredients include vitamins and derivatives thereof, antioxidants, skin soothing and healing agents such as aloe vera extract, allantoin and the like, chelators and sequestrants, skin lightening agents, and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol).

Test Methods

Ultracentrifugation "Third-Phase" Method for Determining Structured Surfactant Stability: The Ultracentrifugation "Third-Phase" Method is used to determine structured surfactant phase stability in a personal cleansing composition. The method involves separation of the composition through ultracentrifugation into separate but distinguishable layers. The personal cleansing composition of the present invention can have multiple distinguishable layers, for example a nonstructured surfactant layer, an opaque structured surfactant layer, a clear "third-phase" layer, and benefit phase layers.

The rapid stability aging protocol is set as follow. Prepare a lipid blend by heating a vessel to 180° F. and add Petrolatum (Quidesa Petrolatum from Quidesa, Mexico) and Hydrobrite 1000 White Mineral Oil (from WITCO, USA) at 65:35 weight ratio. Cool the vessel to 110° F. with slow agitation (200 rpm). Stop agitation and cool the vessel to ambient temperature overnight. Add 36 grams of lipid blend (65/35 Pet/MO) to about 44 grams of the structured surfactant composition. Mix the surfactant and lipid together using a spatula for 5 minutes. Place the mixed sample at 120° F. for 10 days. After rapid aging stability testing, transfer about 4 grams of the composition into a Beckman Centrifuge Tube (11×60 mm). Place the centrifuge tube in a Beckman LE-80 Ultracentrifuge and operate the Ultracentrifuge under the following conditions: 50,000 rpm, 2 hours, and @40° C.

After Ultracentrifugation, determine the third-phase volume by measuring the height of various surfactant phases using an Electronic Digital Caliper (within 0.01 mm) as shown below. An example is shown below for personal cleansing composition comprising Expancel microsphere.

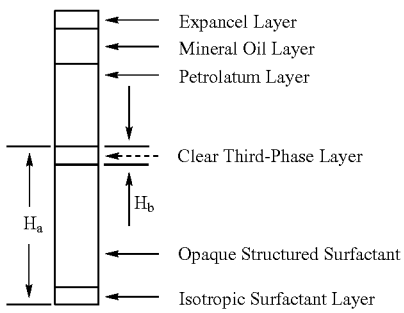

The very top layer is Expancel layer which has the lowest density. The second layer from the top is the clear mineral oil layer. The third layer from the top is the petrolatum layer. The layers below the petrolatum layers contain surfactant/water are determined in the following: $H_a$ is the height of all layers containing surfactant/water and $H_b$ is the height of the clear "third-phase" layer just below the petrolatum layer. It is important to record the readings within 30 minutes after the Ultracentrifugation is finished to minimize material migration across different layers. The third phase volume is calculated as: Third-phase Volume %=$H_b/H_a$*100%

Preferably, the structured surfactant composition comprises less than 20% "third-phase" volume after rapid aging stability protocol. More preferably, the structured surfactant composition comprises less than 15% "third-phase" volume after rapid aging stability protocol. More preferably, the structured surfactant composition comprises less than 10% "third-phase" volume after rapid aging stability protocol. Even more preferably, the structured surfactant composition comprises less than 5% "third-phase" volume after rapid aging protocol. Most preferably, the structured surfactant composition comprises about 0% "third-phase" volume after rapid aging protocol.

Yield Stress and Zero Shear Viscosity Method: The Yield Stress and Zero Shear Viscosity of a phase of the present composition, can be measured either prior to combining in the composition, or after combining in the composition by separating the phase by suitable physical separation means, such as centrifugation, pipetting, cutting away mechanically, rinsing, filtering, or other separation means.

A controlled stress rheometer such as a TA Instruments AR2000 Rheometer is used. The determination is performed at 25° C. with a 4 cm diameter parallel plate measuring system and a 1 mm gap. The geometry has a shear stress factor of 79580 $m^{-3}$ to convert torque obtained to stress.

First a sample of the phase is obtained and placed in position on the rheometer base plate, the measurement geometry (upper plate) moving into position 1 mm above the base plate. Excess phase at the geometry edge is removed by scraping after locking the geometry. If the phase comprises particles discernible to the eye or by feel (beads, e.g.) which are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The determination is performed via the programmed application of a continuous shear stress ramp from 0.1 Pa to 1,000 Pa over a time interval of 5 minutes using a logarithmic progression, i.e., measurement points evenly spaced on a logarithmic scale. Thirty (30) measurement points per decade of stress increase are obtained. Stress, strain and viscosity are recorded. If the measurement result is incomplete, for example if material flows from the gap, results obtained are evaluated and incomplete data points excluded. The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

$$\text{Log(strain)} = m*\text{Log(stress)} + b \quad (1)$$

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., $10^x$ for each x). The predicted strain is compared to the actual strain at each measurement point to obtain a % variation at each point, using Equation (2).

$$\text{\% variation} = 100*(\text{measured strain} - \text{predicted strain})/\text{measured strain} \quad (2)$$

The Yield Stress is the first stress (Pa) at which % variation exceeds 10% and subsequent (higher) stresses result in even greater variation than 10% due to the onset of flow or deformation of the structure. The Zero Shear Viscosity is obtained by taking a first median value of viscosity in Pascal-seconds (Pa-sec) for viscosity data obtained between and including 0.1 Pa and the Yield Stress. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

Ultracentrifugation Method: The Ultracentrifugation Method is used to determine the percent of a structured domain or an opaque structured domain that is present in a multi-phase personal care composition that comprises a surfactant phase comprising a surfactant component. The method involves the separation of the composition by ultracentrifugation into separate but distinguishable layers. The multi-phase personal care composition of the present invention can have multiple distinguishable layers, for example a non-structured surfactant layer, a structured surfactant layer, and a benefit layer.

First, dispense about 4 grams of multi-phase personal care composition into Beckman Centrifuge Tube (11×60 mm). Next, place the centrifuge tubes in an Ultracentrifuge (Beckman Model L8-M or equivalent) and ultracentrifuge using the following conditions: 50,000 rpm, 18 hours, and 25° C.

After ultracentrifuging for 18 hours, determine the relative phase volume by measuring the height of each layer visually using an Electronic Digital Caliper (within 0.01 mm). First, the total height is measured as $H_a$ which includes all materials in the ultracentrifuge tube. Second, the height of the benefit layer is measured as $H_b$. Third, the structured surfactant layer is measured as $H_c$. The benefit layer is determined by its low moisture content (less than 10% water as measured by Karl Fischer Titration). It generally presents at the top of the centrifuge tube. The total surfactant layer height ($H_s$) can be calculated by this equation:

$H_s = H_a - H_b$

The structured surfactant layer components may comprise several layers or a single layer. Upon ultracentrifugation, there is generally an isotropic layer at the bottom or next to the bottom of the ultracentrifuge tube. This clear isotropic layer typically represents the non-structured micellar surfactant layer. The layers above the isotropic phase generally comprise higher surfactant concentration with higher ordered structures (such as liquid crystals). These structured layers are sometimes opaque to naked eyes, or translucent, or clear. There is generally a distinct phase boundary between the structured layer and the non-structured isotropic layer. The physical nature of the structured surfactant layers can be determined through microscopy under polarized light. The structured surfactant layers typically exhibit distinctive texture under polarized light. Another method for characterizing the structured surfactant layer is to use X-ray diffraction technique. Structured surfactant layer display multiple lines that are often associated primarily with the long spacing of the liquid crystal structure. There may be several structured layers present, so that $H_c$ is the sum of the individual structured layers. If a coacervate phase or any type of polymer-surfactant phase is present, it is considered a structured phase.

Finally, the structured domain volume ratio is calculated as follows:

Structured Domain Volume Ratio=$H_c/H_s*100\%$

If there is no benefit phase present, use the total height as the surfactant layer height, $H_s = H_a$.

Method of Use

The multi-phase personal care compositions of the present invention are preferably applied topically to the desired area of the skin or hair in an amount sufficient to provide effective delivery of the skin cleansing agent, hydrophobic material, and particles to the applied surface. The compositions can be applied directly to the skin or indirectly via the use of a cleansing puff, washcloth, sponge or other implement. The compositions are preferably diluted with water prior to, during, or after topical application, and then subsequently the skin or hair rinsed or wiped off, preferably rinsed off of the applied surface using water or a water-insoluble substrate in combination with water. The present invention is therefore also directed to methods of cleansing the skin through the above-described application of the compositions of the present invention.

Method of Manufacture

The multi-phase personal care compositions of the present invention may be prepared by any known or otherwise effective technique, suitable for making and formulating the desired multi-phase product form. It is effective to combine toothpaste-tube filling technology with a spinning stage design. Additionally, the present invention can be prepared by the method and apparatus as disclosed in U.S. Pat. No. 6,213, 166, issued to Thibiant, et al. on Apr. 10, 2001. The method and apparatus allows two or more compositions to be filled in a spiral configuration into a single container using at least two nozzles which fill the container, which is placed on a static mixer and spun as the composition is introduced into the container.

Alternatively, the present invention can be prepared by a method disclosed in commonly owned U.S. patent application Ser. No. 10/837,214 Publication No. 2004/0219119 A1 entitled "Visually distinctive multiple liquid phase compositions" filed by Wei, et al. on Apr. 30, 2004, published on Nov. 18, 2004. The method and apparatus allows two separate compositions to be combined in predetermined amounts, blended into a single resultant composition with visually distinct phases, and filled by one nozzle into a single container that is lowered and rotated during filling.

If the multi-phase personal care compositions are patterned, it can be desirable to package these compositions in a transparent or translucent package such that the consumer can view the pattern through the package. Because of the viscosity of the subject compositions it may also be desirable to include instructions to the consumer to store the package upside down, on its cap to facilitate dispensing.

EXAMPLES

The following example described in Table 3 is non-limiting examples of the multi-phase composition of the present invention.

TABLE 3

| Examples of the Present Invention | |
|---|---|
| Ingredient | wt % |
| I. Structured Surfactant Phase Composition | |
| Sodium Trideceth Sulfate (Cedapal TD-407 from Stepan) | 7.7 |
| Sodium Lauryl Sulfate | 7.7 |
| Sodium Lauroamphoacetate (Miranol L-32 from Rhodia) | 4.6 |
| Guar Hydroxypropyltrimonium Chloride (N-Hance 3196 from Aqualon) | 0.6 |
| Xanthan Gum (Keltrol 1000 from CP Kelco) | 0.2 |
| PEG 90M (Polyox WSR 301 from Dow Chemical) | 0.1 |
| Isosteareth-2 (Hetoxol IS-2 from Global Seven) | 2.0 |
| Expancel (091 DE 40 from Expancel Inc.) | 0.3 |
| Sodium Chloride | 4.25 |
| Disodium EDTA | 0.05 |
| Kathon CG | 0.033 |
| Citric Acid (to pH = 5.8) | 0.4 |
| High ClogP PRM | 1 |
| Water | Q.S. |
| (pH) | (5.8) |
| II. Benefit Phase Composition | |
| Petrolatum (from Quidesa, Mexico) | 65 |
| Hydrobrite 1000 White Mineral Oil (from WITCO) | 34.99 |
| Red 7 Pigment | 0.01 |

The compositions described above can be prepared by conventional formulation and mixing techniques. Prepare the cleansing phase composition by first adding citric acid into water at 1:3 ratios to form a citric acid premix. Prepare a polymer premix by adding Polyox WSR301 and Xanthan Gum into Isosteareth-2. Then, add the following ingredients into the main mixing vessel in the following sequence with agitation: water, N-Hance polymer, Expancel, sodium lauroamphoacetate, sodium trideceth sulfate, sodium sodium lauroamphoacetate, sodium lauryl sulfate, sodium chloride, sodium benzoate, and Disodium EDTA. Add citric acid premix to adjust pH to 5.8. Add the polymer premix into the main mixing vessel with continuous agitation. Add high ClogP PRM and continue agitation until homogeneous.

Prepare the benefit phase composition by first adding petrolatum into a mixing vessel. Heat the vessel to 180° F. (82.2° C.). Then, add Hydrobrite 1000 White mineral oil and cosmetic pigment with agitation. Let the vessel cool down with slow agitation to about 110° F. (43.3° C.) and transfer the lipid to a container to cool down to ambient overnight.

The following examples described in Table 4 and 5 are comparative examples of personal care compositions.

TABLE 4

Comparative Example 1 of a personal care composition not comprising perfume raw materials (PRMs)

| Ingredient | wt % |
|---|---|
| I. Structured Surfactant Phase Composition | |
| Sodium Trideceth Sulfate (Cedapal TD-407 from Stepan) | 7.7 |
| Sodium Lauryl Sulfate | 7.7 |
| Sodium Lauroamphoacetate (Miranol L-32 from Rhodia) | 4.6 |
| Guar Hydroxypropyltrimonium Chloride (N-Hance 3196) | 0.6 |
| Xanthan Gum (Keltrol 1000 from CP Kelco) | 0.2 |
| PEG 90M (Polyox WSR 301 from Dow Chemical) | 0.1 |
| Isosteareth-2 (Hetoxol IS-2 from Global Seven) | 2.0 |
| Sodium Chloride | 4.25 |
| Expancel (091 DE 40 from Expancel Inc.) | 0.3 |
| Disodium EDTA | 0.05 |
| Kathon CG | 0.033 |
| Citric Acid (to pH = 5.8) | 0.4 |
| Water | Q.S. |
| (pH) | (5.8) |
| II. Benefit Phase Composition | |
| Petrolatum (from Quidesa, Mexico) | 65 |
| Hydrobrite 1000 White Mineral Oil (from WITCO) | 34.99 |
| Red 7 Pigment | 0.01 |

The compositions described above can be prepared by conventional formulation and mixing techniques. Prepare the cleansing phase composition by first adding citric acid into water at a 1:3 ratio to form a citric acid premix. Prepare a polymer premix by adding Polyox WSR301 and Xanthan Gum into Isosteareth-2. Then, add the following ingredients into the main mixing vessel in the following sequence with agitation: water, N-Hance polymer, Expancel, sodium lauroamphoacetate, sodium trideceth sulfate, sodium sodium lauroamphoacetate, sodium lauryl sulfate, sodium chloride, sodium benzoate, and Disodium EDTA. Add citric acid premix to adjust pH to 5.8. Add the polymer premix into the main mixing vessel with continuous agitation. Continue agitation until homogeneous.

Prepare the benefit phase composition by first adding petrolatum into a mixing vessel. Heat the vessel to 180° F. (82.2° C.). Then, add Hydrobrite 1000 White mineral oil and cosmetic pigment with agitation. Let the vessel cool down with slow agitation to about 110° F. (43.3° C.) and transfer the lipid to a container to cool down to ambient overnight.

TABLE 5

Comparative Example 2 of a personal care composition comprising PRMs having a ClogP less than 1.8

| Ingredient | wt % |
|---|---|
| I. Structured Surfactant Phase Composition | |
| Sodium Trideceth Sulfate (Cedapal TD-407 from Stepan) | 7.7 |
| Sodium Lauryl Sulfate | 7.7 |
| Sodium Lauroamphoacetate (Miranol L-32 from Rhodia) | 4.6 |
| Guar Hydroxypropyltrimonium Chloride (N-Hance 3196) | 0.6 |
| Xanthan Gum (Keltrol 1000 from CP Kelco) | 0.2 |

TABLE 5-continued

Comparative Example 2 of a personal care composition comprising PRMs having a ClogP less than 1.8

| Ingredient | wt % |
|---|---|
| PEG 90M (Polyox WSR 301 from Dow Chemical) | 0.1 |
| Isosteareth-2 (Hetoxol IS-2 from Global Seven) | 2.0 |
| Sodium Chloride | 4.25 |
| Expancel (091 DE 40 from Expancel Inc.) | 0.3 |
| Disodium EDTA | 0.05 |
| Kathon CG | 0.033 |
| Citric Acid (to pH = 5.8) | 0.4 |
| Low CLogP PRM | 1 |
| Water | Q.S. |
| (pH) | (5.8) |
| II. Benefit Phase Composition | |
| Petrolatum (from Quidesa, Mexico) | 65 |
| Hydrobrite 1000 White Mineral Oil (WITCO) | 34.99 |
| Red 7 Pigment | 0.01 |

The compositions described above can be prepared by conventional formulation and mixing techniques. Prepare the cleansing phase composition by first adding citric acid into water at a 1:3 ratio to form a citric acid premix. Prepare a polymer premix by adding Polyox WSR301 and Xanthan Gum into Isosteareth-2. Then, add the following ingredients into the main mixing vessel in the following sequence with agitation: water, N-Hance polymer, Expancel, surfactants, sodium chloride, sodium benzoate, and Disodium EDTA. Add citric acid premix to adjust pH to 5.8. Add the polymer premix into the main mixing vessel with continuous agitation. Add low ClogP PRM and continue agitation until homogeneous.

Prepare the benefit phase composition by first adding petrolatum into a mixing vessel. Heat the vessel to 180° F. (82.2° C.). Then, add Hydrobrite 1000 White mineral oil and cosmetic pigment with agitation. Let the vessel cool down with slow agitation to about 110° F. (43.3° C.) and transfer the lipid to a container to cool down to ambient overnight.

Stability Results:

Structured surfactant phase stability is determined through Ultracentrifugation "Third-Phase" Method as discussed in the Test Methods section above. A composition is prepared by hand-mixing structured surfactant phase comprising a PRM or mixture of PRMs and a benefit phase at 55:45 w/w ratio for 3 minutes vigorously by hand in a 4 oz. jar. The mixture is capped and placed at 120° F. (48.9° C.) for 10 days. After 10 days, a compositionally homogenous aliquot of the mixture is removed and ultracentrifuged. Phase stability is measured after ultracentrifugation at 50,000 rpm for 2 hours at 40° C. The third phase volume is measured. The results are listed in the Table below for an Example surfactant of the Present invention comprising 1% of individual PRM, combined with 45% of a petrolatum benefit phase.

TABLE 6

Structured Phase stability results for Examples of the Present Invention and Comparative Examples

| Example | PRM in Composition | ClogP | Third Phase Volume |
|---|---|---|---|
| Example of the Present Invention | 1% Gamma-Nonalactone | 1.85 | 0.4% |
| Example of the | 1% Florol | 2.00 | 0.6% |

TABLE 6-continued

Structured Phase stability results for Examples of the Present Invention and Comparative Examples

| Example | PRM in Composition | ClogP | Third Phase Volume |
|---|---|---|---|
| Present Invention Example of the Present Invention | 1% Isoeugenol | 2.45 | 0.9% |
| Example of the Present Invention | 1% Cis Jasmone | 2.91 | 1% |
| Example of the Present Invention | 1% Dihydromyrcenol | 3.00 | 0% |
| Example of the Present Invention | 1% Citral | 3.17 | 0.8% |
| Example of the Present Invention | 1% Geraniol | 3.28 | 0% |
| Example of the Present Invention | 1% Linalool | 3.28 | 2.2% |
| Example of the Present Invention | 1% Citronellol | 3.38 | 0% |
| Example of the Present Invention | 1% Cymal | 3.72 | 1% |
| Comparative Example 1 | No PRM | — | 9% |
| Comparative Example 2 | 1% Dipropylene Glycol | −0.69 | 33.4% |
| Comparative Example 2 | 1% Hydroxycitronellal | 1.54 | 17.3% |
| Comparative Example 2 | 1% Ethyl Maltol | 1.70 | 37.7% |
| Comparative Example 2 | 1% Ethyl Vanillin | 1.72 | 52.8% |

The results show that the comparative examples 1 and 2 of personal care compositions are less stable due to formation of high third phase volume. The structured surfactant compositions of the present invention show improved phase stability due to lower third phase volume.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of stabilizing a multiphase composition comprising a structured surfactant phase having a Structured Domain Volume Ratio greater than about 40%, a benefit phase and perfume comprising perfume raw materials; said method comprising the steps of selecting at least 70%, by weight of said perfume, of said perfume raw materials having a ClogP of greater than 1.8; and adding said perfume raw materials to said composition.

2. The method of claim 1 wherein at least 80% of said perfume raw materials have a ClogP of greater than 1.8.

3. The method of claim 1 wherein at least 85% of said perfume raw materials have a ClogP of greater than 1.8.

4. The method of claim 1 wherein at least 90% of said perfume raw materials have a ClogP of greater than 1.8.

5. The method of claim 1 wherein at least 95% of said perfume raw materials have a ClogP of greater than 1.8.

6. The method of claim 1 further comprising the step of incorporating a preservative into said multiphase composition wherein said preservative is substantially free of formaldehyde.

7. The method of claim 6 wherein said preservative comprises less than 0.01% formaldehyde.

8. A multiphase personal care composition comprising a structured surfactant phase having a Structured Domain Volume Ratio greater than about 40%, a benefit phase and perfume comprising perfume raw materials; wherein at least 70%, by weight of said perfume, of said perfume raw materials have a Clog P of greater than 1.8.

9. The multi-phase, personal care composition of claim 8, wherein said personal care composition is selected from the group consisting of a skin care lotion, a bar soap, a body wash, a shampoo, conditioner, a in-shower body moisturizer and mixtures thereof.

10. The multi-phase, personal care composition of claim 8, wherein said benefit phase has a Consistency Value (K) of from about 30 to about 350 Pa-s.

11. The multi-phase, personal care composition of claim 8, wherein said structured surfactant phase is visually distinct from said benefit phase.

12. The multi-phase, personal care composition of claim 11 wherein said structured surfactant phase and benefit phase form a pattern.

13. The multi-phase, personal care composition of claim 12, wherein said pattern is selected from the group consisting of striped, geometric, marbled, and combinations thereof.

14. A personal care composition comprising a structured surfactant phase having a Structured Domain Volume Ratio greater than about 40%, a benefit phase, a preservative, and perfume comprising perfume raw materials; said preservative being substantially free of formaldehyde; wherein at least 70%, by weight of said perfume, of said perfume raw materials have a Clog P greater than 1.8.

15. A personal care composition comprising a structured surfactant phase having a Structured Domain Volume Ratio greater than about 40%, a benefit phase and perfume comprising perfume raw materials; wherein at least 70%, by weight of said perfume, has a ClogP of greater than 1.8; and wherein less than 30%, by weight of said perfume, of said perfume raw materials are selected from the group consisting of benzaldehyde dimethyl acetal, benzaldehyde glyceryl acetal, cinnamic alcohol, cinnamic aldehyde dimethyl acetal, cis-3- hexenal, diethyl malonate, dihydro coumarin, ethyl butanoate, ethyl methyl dioxolane acetate (2-Me, 1,3-dioxol-2-acetate),ethyl vanillin, 4-hydroxy-3-ethoxybenzaldehyde, heliotropine dimethyl acetal, hexanol (2-, 3-), hexenol (all isomers), hexenone (1-hexen-3-one, 4-hexen-3-one, 5-hexen-2-one), hexyl cinnamate, hydrocinnamic aldehyde, hydrocinnamyl alcohol, hydroquinone, hydroquinone monomethyl ether, linalool oxide, methyl phenylacetate, nonenal (all isomers), o-anisaldehyde, m-anisaldehyde, and p-anisaldehyde, phenethyl alcohol, phenoxyacetaldehyde, phenylacetaldehyde ethyleneglycol acetal, prenyl acetate, propylene glycol, sinensal, triethyl citrate, valeraldehyde, valeric acid, valerolactone, vanillic acid, vanillin acetate, vanillin isobutyrate, vanillyl alcohol, vanillylidene acetone and mixtures thereof.

16. The personal care composition of claim 15, wherein said composition is multiphase.

17. The personal care composition of claim 16, wherein said 95% of said perfume raw materials have a Clog P greater than 1.8.

18. The personal care composition of claim 16, wherein said structured surfactant phase is visually distinct from said benefit phase.

19. The personal care composition of claim 15 wherein said personal care composition further comprises a preservative wherein said preservative being substantially free of formaldehyde.

20. The personal care composition of claim 15, wherein said personal care composition is selected from the group consisting of a skin care lotion, a bar soap, a body wash, a shampoo, conditioner, a in-shower body moisturizer and mixtures thereof.

* * * * *